US006475161B2

(12) United States Patent
Teicher et al.

(10) Patent No.: US 6,475,161 B2
(45) Date of Patent: Nov. 5, 2002

(54) METHODS FOR DIAGNOSING ALZHEIMER'S DISEASE AND OTHER FORMS OF DEMENTIA

(75) Inventors: Martin H. Teicher, Rye, NH (US); Steven B. Lowen, Burlington, MA (US); David G. Harper, Cambridge, MA (US); Sumer D. Verma, Lexington, MA (US); Janet M. Lawrence, Newton, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 09/823,030

(22) Filed: Mar. 29, 2001

(65) Prior Publication Data

US 2002/0143240 A1 Oct. 3, 2002

(51) Int. Cl.[7] .................................................. A61B 5/00
(52) U.S. Cl. ...................................... 600/558; 600/300
(58) Field of Search ............................... 600/300, 558, 600/587, 595

(56) References Cited

U.S. PATENT DOCUMENTS

| | | | | |
|---|---|---|---|---|
| 4,984,578 A | | 1/1991 | Keppel et al. ............... | 128/732 |
| 4,987,903 A | | 1/1991 | Keppel et al. ............... | 128/732 |
| 5,150,716 A | | 9/1992 | Franssen et al. ............ | 128/774 |
| 5,249,581 A | * | 10/1993 | Horbal et al. ................ | 600/595 |
| 5,695,343 A | | 12/1997 | Jabourian .................... | 434/236 |
| 5,801,810 A | | 9/1998 | Roenker ...................... | 351/246 |
| 5,940,801 A | | 8/1999 | Brown .......................... | 705/2 |
| 5,956,125 A | | 9/1999 | Rosse et al. ................. | 351/221 |
| 6,032,119 A | * | 2/2000 | Brown et al. ............... | 600/300 |
| 6,053,866 A | | 4/2000 | McLeod ...................... | 600/300 |
| 6,066,015 A | * | 5/2000 | Guillen ........................ | 600/595 |
| 6,067,986 A | * | 5/2000 | Kluger et al. ............... | 600/595 |
| 6,228,038 B1 | * | 5/2001 | Claessens ................... | 600/558 |

OTHER PUBLICATIONS

Ferris et al., "NYU Computerized Test Battery for Assessing Cognition in Aging and Dementia," *Psychopharmacology Bulletin* 24: 699–702, 1988.
Flicker et al., "Mild Cognitive Impairment in the Elderly: Predictors of Dementia," *Neurology* 41:1006–1009, 1991.
Greenberg, "An Objective Measure of Methylphenidate Response: Clinical Use of the MCA," *Psychopharmacology Bulletin* 23:279–282, 1987.
Paulus et al., "The Effects of MDMA and Other Methylenedioxy–Substituted Phenylalkylamines on the Structure of Rat Locomotor Activity," *Neuropsychopharmacology* 7:15–31, 1992.
Reisberg et al., "The Global Deterioration Scale for Assessment of Primary Degenerative Dementia," *Am. J. Psychiatry* 139:1136–1139, 1982.
Rosvold et al., "A Continuous Performance Test of Brain Damage," *Journal of Consulting and Clinical Psychology* 20:343–350, 1956.
Teicher et al., "Objective Measurement of Hyperactivity and Attentional Problems in ADHD," *J. Am. Acad. Child Adolesc. Psychiatry* 35:334–342, 1996.

* cited by examiner

*Primary Examiner*—Max Hindenburg
(74) *Attorney, Agent, or Firm*—Clark & Elbing LLP

(57) ABSTRACT

Provided are methods for diagnosing the presence, type, or severity of a dementia in a human subject. The methods involve using a computer-based system to assess impairment of certain cognitive and motor functions that are indicative of Alzheimer's disease and other forms of dementia.

17 Claims, 1 Drawing Sheet

METHODS FOR DIAGNOSING ALZHEIMER'S DISEASE AND OTHER FORMS OF DEMENTIA

FIELD OF THE INVENTION

The invention relates to methods of diagnosing the presence, type, or severity of a dementia.

BACKGROUND OF THE INVENTION

Alzheimer's disease ("AD") is a degenerative brain disorder that afflicts millions of people worldwide. It is the most common form of dementia and can affect memory, mood, personality, and cognitive ability. The risk of developing AD becomes greater with age. As the average human life-span continues to increase, the number of people developing AD at some point in their lives is escalating rapidly. Currently, an estimated 1 in 20 people over the age of 65 are affected by some form of dementia. In persons over the age of 80, that number rises to 1 in 5.

The effects of AD can be devastating. Early symptoms include forgetfulness, learning difficulties, and loss of concentration. The later stages of the disease are characterized by disorientation, extreme memory loss, impairment of speech and reading comprehension, and changes in personality. Dramatic mood swings can occur, including outbursts of anger, bouts of fearfulness, and periods of deep apathy or depression. The sufferer becomes increasingly confused, particularly when confronted with unfamiliar settings, and may wander off and become lost. Physical problems, such as an odd gait, a loss of coordination, an inability to chew and swallow, and an inability to control bowel and bladder functions, gradually develop. Eventually, the patient may become totally noncommunicative, physically helpless, and incontinent. The disease is invariably fatal.

AD can also have a profound impact on the relatives of the person suffering from the disease. About seventy percent of AD patients are cared for at home by family members. In the early and middle stages of AD, patients may need help in managing their financial and business affairs. As the disease progresses, the affected person becomes steadily more dependent on caregivers to help perform daily tasks. The patient's mental functioning eventually deteriorates to the point where it is not safe to leave the person unattended. Ultimately, the disease may leave its victims bedridden and unable to care for themselves. Under these circumstances, AD can take a tremendous physical, financial, and emotional toll on the caregivers.

Although there is currently no cure for AD, early diagnosis is important for a number of reasons. For instance, it is crucial to rule out other conditions which have symptoms that are similar to AD, but which are treatable. In addition, the patient and family members can receive much help and advice from doctors and other professionals in coping with this disease. Furthermore, medications are available which can help relieve some of the common symptoms of AD, including depression, anxiety, and sleep disturbance. There is also hope that treatments may be developed in the future which will slow or halt the progression of the disease, making early detection and intervention even more vital.

Diagnosing AD can often be difficult, especially in the early stages, because many of the symptoms of the disease mirror the natural signs of aging. In some situations, a definitive diagnosis may not be possible until the patient has died and an autopsy can be performed. There are also several forms of dementia that appear superficially similar to AD, but have distinct underlying pathological processes. These dementias are often indistinguishable from AD using conventional testing techniques.

Current psychological tests for AD that are used clinically focus on deteriorations in memory, particularly in short-term or "working" memory. In general, the disorder must be fairly well advanced before significant impairments in memory are observed. Consequently, these tests are not fully capable of diagnosing AD in the early stages. Thus, there is a need for an easily administered, non-invasive, and reliable test for detecting AD while still in the early stages of development.

SUMMARY OF THE INVENTION

The regions of the brain that mediate working memory also regulate the capacity for sustained attention (i.e., vigilance), control of impulses, and motor activity. We believe that, in patients suffering from AD and other dementias, impairment of these functions often occurs prior to detectable changes in memory. We posit that testing a patient for disturbances in attention, impulsiveness, and/or motor function can lead to early diagnosis of AD and other forms of dementia. Earlier diagnosis, in turn, makes it possible to begin treating the underlying disorder while still in the early stages, in order to halt or slow its progression.

Accordingly, the present invention provides a method of diagnosing the presence, type, or severity of a dementia in a human subject using computerized testing, which method includes the steps of: (a) placing, in proximity to the subject, a monitor that is connected to a computer, and a device that is controllable by the subject and that is also connected to the computer; (b) presenting the subject with instructions for activating the device in response to visual images on the monitor; (c) presenting to the subject one or more visual images on the monitor; (d) storing in the computer the instances of device activation by the subject; and (e) scoring the accuracy or response time, or both, of device activation, wherein scoring below a pre-determined level is diagnostic for dementia. Alternatively, more complex measures of subject response patterns may be analyzed.

In one embodiment of the invention, the method further includes the steps of: (f) using a motion analysis device connected to the computer to record the movements of the subject during presentation of the visual images; (g) storing the record of these movements in the computer; (h) analyzing the recorded movements for deviations from pre-determined norms; and (i) using the analysis of step (h) together with the scoring of step (e) in diagnosing dementia. The motion analysis device is preferably an infrared camera capable of detecting small infrared reflective markers. These markers can be placed at various positions on the subject, such as the head, elbow, and shoulders, in order to monitor the movements of these portions of the subject's body.

The method of the invention can be used to diagnose and distinguish various forms of dementia, including dementia associated with Alzheimer's disease, frontotemporal degenerative dementias (e.g., Pick's disease, corticobasal ganglionic degenerations, and frontotemporal dementia), Huntington's disease, Creutzfeldt Jakob disease, Parkinson's disease, cerebrovascular disease, head trauma, and substance abuse).

Other features and advantages of the invention will be apparent from the following detailed description and from the claims.

BRIEF DESCRIPTION OF THE DRAWING

The FIGURE is a schematic diagram illustrating a computerized system that provides diagnostic information for assessing the presence or degree of a dementia.

DETAILED DESCRIPTION

Figure 1:
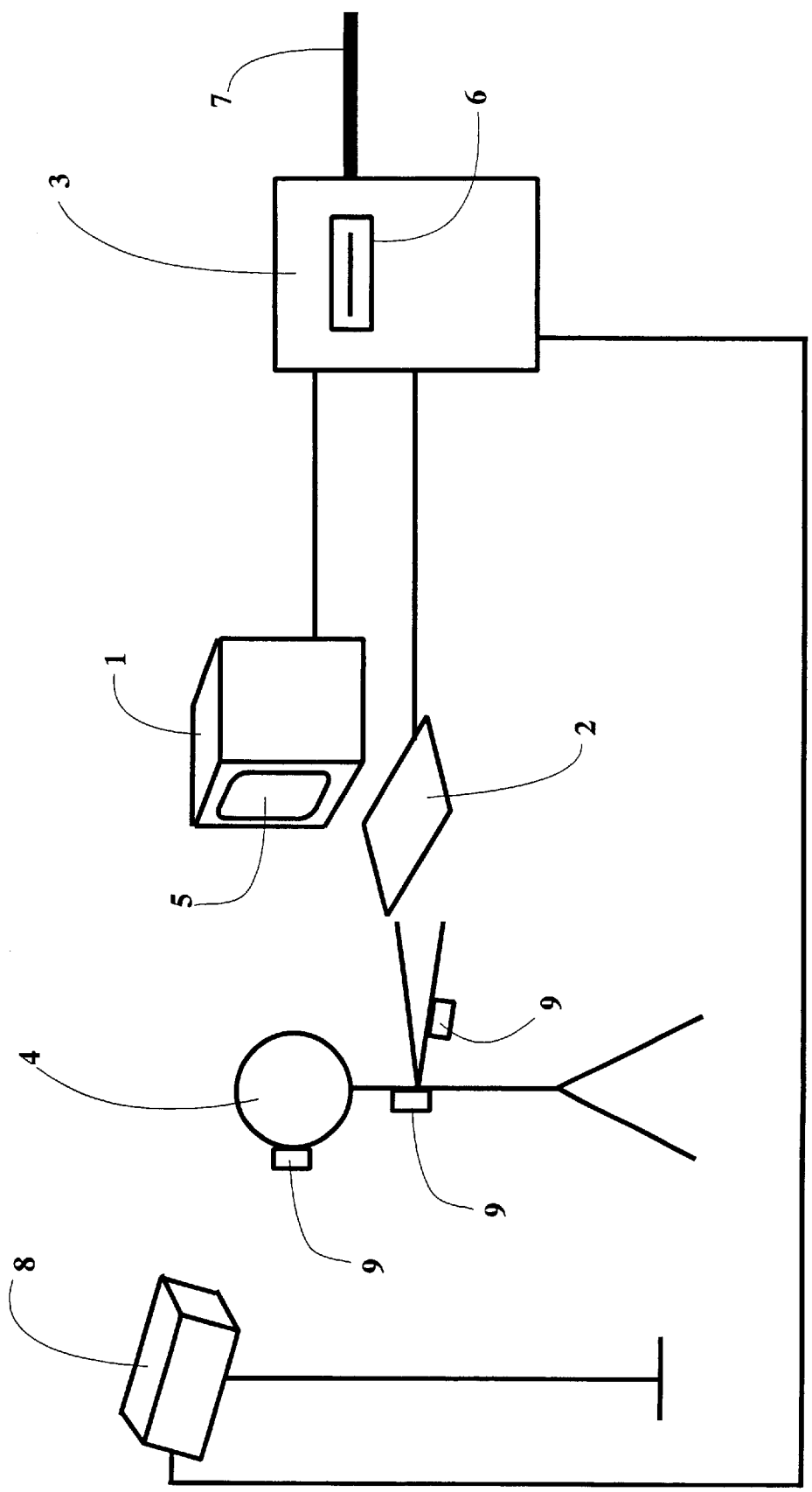

The present invention features a method for diagnosing the presence or severity of a dementia in a human subject. The method utilizes a computer-based system to assess impairment of certain cognitive and motor functions that are indicative of AD and other forms of dementia.

An embodiment of the invention is shown in the FIGURE. The system includes a monitor 1 that is a capable of displaying visual images on a screen 5.

The monitor 1 is attached to a computer 3 and is positioned in proximity to a subject 4, so that the subject 4 may view the images displayed on the monitor screen 5. The computer 3 can be programmed to display a desired sequence of images, to which the subject 4 is instructed to respond by activating an input device 2 that is also attached to the computer 3 and is controllable by the subject 4. The input device 2 can be, for example, a standard computer keyboard, a hand-held plunger switch, or a large, easy-to-hit switch several (2–3) inches in length. When activated, the input device 2 sends the subject's inputs to the computer 3 which stores and analyzes the incidents of device activation.

The system may also include a motion analysis device 8 that is connected to the computer 3 and positioned so as to record the movements of the subject 4. Any video camera or other motion-sensing device capable of detecting the movements of the subject 4 can be used. For instance, the motion analysis device 8 can be an infrared motion analysis system (e.g., Qualisys, Glastonbury, CT) that includes a high-resolution CCD infrared video camera, an infrared strobe, and a video processor that provides hardware analysis of the video signal and outputs data to the computer 3. Such infrared motion analysis systems are known in the art, and are specifically designed to detect and record the precise vertical and horizontal position of small, light-weight infrared reflective markers 9. These markers 9 are attached to the subject 4 at various points, such as the head, shoulders, and elbows. As the subject 4 moves these portions of his or her body, the IR motion analysis system detects changes in the positions of the markers 9 and relays this information to the computer 3. Successive marker coordinates can be stored in the computer 3 and analyzed using commercially available software (e.g., OPTAX software, OptaxSystems, Inc., Burlington, Mass.).

The computer 3 can be a stand-alone personal computer, preferably with high computational capacity microprocessors. Alternatively, a minicomputer or mainframe computer can be used. The computer 3 can have a disc drive 6 into which the software that analyzes the subject's input's and/or movement patterns is loaded. In a preferred embodiment, the computer 3 has a connection 7 to a network of computers, such as the Internet. This allows the computer 3 to exchange data with other computers connected to the network. Thus, a subject may be tested not only in a clinical setting, but also at a remote location, such as the home, school, or workplace, thereby eliminating the inconvenience of traveling long distances for testing.

The system of the invention can be used to test certain cognitive and psychomotor functions that are diagnostic of AD and other forms of dementia. For instance, the capacity for sustained attention, control of impulses, reaction time, and regulation or inhibition of motor activity may be impaired in patients suffering from dementia. Thus, by measuring these functions it is possible to distinguish normal patients from those with dementia, and even identify the type of dementia the patient is experiencing. The system can also be used to monitor these functions at different stages of the disease in order to track its development and progression.

Attention and Reaction Time

One way the system can be used to assess attention and reaction time is by providing the subject with a continuous performance task ("CPT") and recording the subject's performance. A typical CPT involves presenting the subject with a series of stimuli and instructing the subject to respond only to certain target stimuli. The subject's performance is scored based on the number of target stimuli correctly identified, the number of target stimuli missed, the number of responses to non-target stimuli, the number of non-target stimuli correctly missed, and the response time (e.g., U.S. Pat. No. 5,940,801).

For example, a subject's visual attention can be tested by displaying a series of visual stimuli on a computer screen, for which different responses are required of the subject. The stimuli can be any sort of visual image, including but not limited to, individual symbols, numbers, letters, or shapes, or a combination thereof. In one version of this test, the images are of two types and the subject is instructed to respond to only one type by activating the input device when the target stimuli appears on the screen. Typically, the test requires the subject to distinguish between two similar visual images, such as a five-pointed star and an eight-pointed star (see, e.g., Greenberg (1987), *Psychopharmacol. Bull.* 23:279–282 and Rosvold et al. (1956), *J. Consulting and Clinical Psychology* 20:343–350). For instance, the subject is instructed to press the space bar on the computer's keyboard if an eight-pointed star is displayed on the computer screen, and to do nothing when a five-pointed star appears on the screen. Data are collected for each individual image presentation, including the type of stimulus (e.g., five-pointed star or eight-pointed star), whether or not the subject responded, and, if so, the amount of time the subject took to respond. From this raw data, the percentage of correct responses to the target stimulus, percentage of correct passes to the non-target stimulus, average response time, response time variability, and other statistics may be obtained. In addition, as is discussed below, a motion analysis device can be used to detect and record the subject's movement patterns throughout the test. At the end of the test, the recorded data (e.g., key press information and movement information) can be processed by the computer or transmitted over an Internet connection to a central processing station, where a report is generated and transmitted back to the testing site (e.g., U.S. Ser. No. 60/243,963).

Another CPT for assessing a subject's visual attention capabilities involves measuring the duration of time a particular visual stimulus must be present after a period of no stimulus before a subject can detect and respond to it (e.g., U.S. Pat. No. 5,801,810). For example, overall reaction time is estimated by presenting either a particular shape, such as a circle, or no stimulus (i.e., a blank screen) in random fashion. The subject is instructed to activate the input device as soon as possible after the circle appears on the screen, but not before. For both circle and no stimulus presentations, the percentage correct, the average response time, and variations about that average are stored, and provide a means for assessing deterioration in visual attention (See U.S. Ser. No. 60/204,663).

These CPTs may be used alone, together, or in conjunction with other well-known psychological tests for determining attention and reaction time. In one embodiment of the invention, the subject is asked to perform a series of CPTs starting with the circle/no stimulus CPT described above, followed by a CPT that requires the subject to distinguish between two different types of the same basic shape (e.g., five-pointed stars and eight-pointed stars). Testing of the subject's performance may be conducted with or without providing corrective feedback to the subject during performance of the CPT.

Motor Activity

Using the system of the invention, the movement abnormalities of a person with AD can be objectively discerned by measuring the frequency, amplitude, and pattern of body movements. As discussed above, very precise measurements of a subject's movements can be made using a motion analysis system that includes an infrared camera and one or more infrared reflective markers placed on the subject. These systems typically have a high spatial resolution (e.g. 40 µm) and can simultaneously track the vertical and horizontal movements of as many as 20 IR reflective markers. By using multiple IR cameras, it is possible to track the three-dimensional movements of the markers, if so desired.

Generally, the motor activity of the subject is monitored during performance of a CPT, such as those described above. Data is collected and sent to a computer to determine the time spent moving, number of movements, total distance and area traveled, and certain spatiotemporal measures of movement complexity. The computer, in addition to including the software required for running the CPT, contains software that performs the processing and analysis of the movement data (e.g. OPTAX Software).

Movement patterns of the subject can be analyzed using, for example, the procedures described in Paulus, M., Geyer, M. (1992), *Neuropsychopharmacology* 7:15–31 and Teicher et al. (March 1996), *J. Am. Acad. Child Adolsec. Psychiatry* 35(3): 334–342, which are based on the concept of microevents. A new microevent begins whenever the marker moves more than a predetermined distance (e.g., 1.0 mm or more) from the location of the previous microevent, and is defined by its position and duration. From the sequence of microevents, the mean locomotor path length can be calculated, along with two scaling exponents. The first exponent, the spatial scaling exponent, is a measure of the complexity of the movement and is calculated by ascertaining the logarithmic rate of information decay at progressively lower levels of resolution. Conceptually, if a marker is still or moving in a straight line, no information is lost if the marker's position is sampled less frequently. The total distance traversed can still be calculated. On the other hand, if a marker is moving in a convoluted path, then less frequent sampling smooths out the route and underestimates the distance traveled. Spatial complexity corresponds to the concept of fractal dimensions and ranges from 1.0 (straight line movement) to 2.0 (complex, convoluted movement patterns).

The other exponent, known as the temporal scaling exponent, is calculated from the log-log relationship between the frequency of the microevents and their duration. For a two-process model in which a marker is either in motion or immobile, stochastic theory dictates that there will be a greater number of brief periods of immobility than long periods of immobility (though not necessarily a greater amount of time). The log-log relationship provides a robust measure of relative activity versus inactivity and indicates the degree to which a subject is moving in the environment.

Since humans suffering from dementia exhibit abnormal motor activity and impaired cognitive functioning, the data collected concerning a subject's movement patterns and CPT performance can be compared to those of demented and non-demented patients to determine whether the subject has dementia. If so, the data can be used to ascertain not only the severity of the dementia, but also its etiology, thereby allowing the attending physician to determine the most appropriate course of treatment.

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein.

All publications, patents, and patent applications mentioned in this specification are hereby incorporated by reference.

What is claimed is:

1. A method of diagnosing the presence, type, or severity of a dementia in a human subject, said method comprising the steps of:
   (a) placing, in proximity to said subject, (i) a monitor that is connected to a computer, and (ii) a device that is controllable by said subject and that is also connected to said computer;
   (b) presenting to said subject instructions with respect to activating said device in response to visual images on said monitor;
   (c) presenting to said subject one or more of said visual images on said monitor;
   (d) storing in said computer the instances of device activation by said subject; and
   (e) scoring the accuracy or response time, or both, of device activation, wherein scoring below a predetermined level is diagnostic for dementia.

2. The method of claim 1, wherein said method further comprises the steps of:
   (f) using a motion analysis device connected to said computer to record the movements of said subject during presentation of said visual images;
   (g) storing the record of said movements in said computer;
   (h) analyzing said recorded movements for deviations from predetermined norms; and
   (i) using the analysis of step (h) together with the scoring of step
   (e) in diagnosing dementia.

3. The method of claim 1, wherein said dementia is associated with Alzheimer's Disease, frontotemporal degenerative dementias, Huntington's Disease, Creutzfeldt Jakob disease, Parkinson's disease, cerebrovascular disease, head trauma, or substance abuse.

4. The method of claim 3, wherein said dementia is associated with Alzheimer's Disease.

5. The method of claim 2, wherein said motion analysis device is a video camera.

6. The method of claim 5, wherein said camera is an infrared camera capable of detecting an infrared reflective marker.

7. The method of claim 6, wherein at least one infrared reflective marker is placed onto said subject.

8. The method of claim 7, wherein said marker is positioned on the head of said subject.

9. The method of claim 7, wherein at least three markers are placed onto said subject.

10. The method of claim 9, wherein said markers are positioned on the head, elbow, and shoulders of said subject.

11. The method of claim 1, wherein said computer is connected to a second computer via the Internet or other computer network and said instructions or said images are conveyed to said subject across the Internet.

12. The method of claim 2, wherein said movements are recorded while said subject is performing a continuous performance task.

13. The method of claim 1, wherein said visual images are selected from the group consisting of symbols, numbers, letters, and shapes.

14. The method of claim 13, wherein said subject is instructed to activate said device when a specified image is displayed on said monitor.

15. The method of claim 13, wherein said visual images are stars.

16. The method of claim 15, wherein said visual images are five-pointed stars and eight-pointed stars.

17. The method of claim 15, wherein said subject is instructed to activate said device when a star having a specified number of points is displayed on said monitor.

* * * * *